United States Patent [19]
Eberle

[11] Patent Number: 5,318,749
[45] Date of Patent: Jun. 7, 1994

[54] CENTRIFUGATION CHAMBER FOR LIQUOR TESTING

[75] Inventor: Günter Eberle, Tuttlingen, Fed. Rep. of Germany

[73] Assignee: Firma Andreas Hettich, Tuttlingen, Fed. Rep. of Germany

[21] Appl. No.: 882,173

[22] Filed: May 13, 1992

[30] Foreign Application Priority Data

May 14, 1991 [DE] Fed. Rep. of Germany ... 9107153[U]

[51] Int. Cl.⁵ .............................. G01N 9/30
[52] U.S. Cl. ..................... 422/72; 422/81; 422/82; 422/101; 422/102; 436/45; 436/46
[58] Field of Search ............ 422/72, 81, 82, 102, 422/101; 436/45, 46

[56] References Cited

U.S. PATENT DOCUMENTS

| | | | |
|---|---|---|---|
| 3,071,316 | 1/1963 | Piemonte et al. | 422/72 |
| 4,591,486 | 5/1986 | Eberle | 422/72 |
| 4,612,873 | 9/1986 | Eberle | 118/52 |
| 4,670,003 | 6/1987 | Moroz | 494/10 |
| 4,690,670 | 9/1987 | Nielsen | 494/16 |
| 4,853,188 | 8/1989 | Toya | 422/104 |
| 4,865,812 | 9/1989 | Kuntz et al. | 422/72 |
| 4,874,102 | 10/1989 | Jessop et al. | 215/273 |
| 4,902,270 | 2/1992 | Comeau et al. | 494/16 |
| 5,008,083 | 4/1991 | Dickie et al. | 422/101 |
| 5,084,240 | 1/1992 | Babson | 422/72 |

FOREIGN PATENT DOCUMENTS

2089063 6/1982 United Kingdom .

Primary Examiner—James C. Housel
Assistant Examiner—Harold Y. Pyon
Attorney, Agent, or Firm—Lackenbach Siegel Marzullo Aronson & Greenspan

[57] ABSTRACT

The centrifugation chamber serves in particular for liquor testing, the liquid to be tested being arranged in a vessel whose bottom area is formed by a slide retained in a bottom part, there being arranged at least at the outer circumference of the vessel a suction element which lies on the lower part. The upper part is clampable on the lower part by means of a clamping device, so that different size upper parts can be used with a single lower part.

9 Claims, 7 Drawing Sheets

CENTRIFUGATION CHAMBER FOR LIQUOR TESTING

BACKGROUND OF THE INVENTION

The present innovation relates to a centrifugation chamber. Such a centrifugation chamber is used preferably for testing liquid (cerebrospinal fluid). In the cytological testing of such fluids the problem is that there are in the fluid to be tested only relatively few cells that constitute the test object. It is crucial, therefore, to produce a sediment of the cells with a slide, with little loss of cell material in this process as well as in the subsequent processes, as e.g. staining of the sediment sample or fixing of the sediment sample.

In the past, a number of centrifugation chambers have been proposed.

Such a known centrifugation chamber consists of an upper part, which is designed in the manner of a tubule, and which is filled with the liquid to be tested.

This upper part is pressed under the load of a weight onto a lower part, a slide being placed on the bottom surface of the lower part. Between the slide and the upper part is a filter paper or other sorption material. In the following, this sorption material is referred to as filter paper, to simplify matters.

In the area of the circular opening for placing the upper part on the slide, the filter paper is cut out circularly, and this with a diameter such that the sealing edge of the upper part sits on an annular zone of the filter material. As a result, the liquid to be tested, with which the upper part is filled, stands on the slide in the manner of a liquid column, covering an annulus-shaped zone of the filter material as well.

For the sedimentation of the cells to be tested, a so-called spontaneous sedimentation is employed, that is, the centrifugation chamber filled with the test fluid is left standing still for a certain period of time, so that the heavier cell components sink to the bottom in the suspension by gravity and deposit on the circular zone of the slide.

Then the contact pressure of the upper part against the lower part is reduced, so that over the sedimented sample the remaining residual fluid has easier access to the filter material, which filter material absorbs the fluid until the filter material is saturated and the sedimentation field is free of test fluid.

Such a centrifugation chamber has proved successful, but has the disadvantage that because of the spontaneous sedimentation only little cell precipitate is obtainable, and also the sedimentation requires a long period of time.

Another major disadvantage of the known centrifugation chamber is that one cannot combine different size upper parts that can be filled with different volumes of fluid with always the same lower part. The usability of such a centrifugation chamber is thus limited. Besides, the retention of the filter material on the slide is insufficiently solved, in that on the one hand the filter material may slip as the centrifugation chamber is being closed, that is, as the upper part is being clamped on the lower part, and secondly the filter material is not reusable.

SUMMARY OF THE INVENTION

It is therefore the object of the present innovation to develop a centrifugation chamber of the initially mentioned kind so as to provide universal usability, so that such a centrifugation chamber can be filled with different volumes of sample and that furthermore the filter material is reusable.

For the solution of the problem posed, the innovation is characterized by the technical teachings set forth below.

It is an essential feature of the present innovation that the seating zone in the lower part for seating the upper part in this lower part is substantially larger (has a larger diameter) than does by comparison the upper part to be clamped into the lower part.

This makes it possible to clamp onto one and the same lower part a plurality of different upper parts, which may have different filling volumes.

With the given technical teaching there results the additional essential advantage that because of the diameter difference between the upper part and the opening for receiving the upper part in the lower part there forms in the lower part an annular space in the lower part which annularly surrounds the upper part held in the lower part.

By the creation of this annular space in the lower part, disposed radially external of the upper part, the advantage is obtained that in this annular space there can now be arranged a filter material (sorption material) which can be of relatively large volume and due to its large volume has a strong suction capacity.

In this annular space the filter material is now placed and preferably detachably connected with the upper part, so that as the upper part is being removed from the lower part, this filter material stays on the upper part and can be replaced if desired. As has been stated above, the height of the annular space has been chosen relatively great, so as to accommodate therein a filter material of large volume.

It has now been found that as preferred suction material (sorption material) a reusable nonwoven pad can be used which has the form of an annulus and is disposed in this annular space, being snapped onto the lower edge of the upper part. This pad is made e.g. in the manner of a chamois material and hence can be washed, dried, and reused.

With the creation of such a centrifugation chamber it is now possible not only to accelerate the sedimentation process, but also a number of additional advantages are connected therewith.

The sedimentation process is accelerated by the fact that the entire centrifugation chamber is now provided for insertion in the suspension of a centrifuge.

A complete work cycle then takes place as follows:

The centrifugation chamber is assembled by placing a slide on the bottom of the lower part. The underside of the upper part is provided with the annulus-shaped filter material by snapping this filter material onto the lower part. Then the upper part is clamped onto the lower part, several forms of realization being claimed as essential to the invention as clamping means. These various forms of realization will be described later on.

The upper part thus clamped onto the lower part is then filled with the sample fluid from the top. The filled centrifugation chamber is then inserted in the suspension of a centrifuge and the centrifuge is operated until an evaluable sediment has deposited on the slide.

Then the centrifuge is turned off, and the upper part is slightly loosened from the lower part, so that the clamping force between the two parts is somewhat reduced. Owing to this, the left-over fluid parts of the sample fluid now get into the annular gap between the bottom edge (seal lip) of the upper part and the filter material, which is now relieved of the sealing pressure and thereby develops a very high suction capacity. The liquid, therefore, is sucked through this annular gap into the radially external filter material, whereby now the entire test field (sediment field) becomes free and dry.

What is important here is that the drying process is substantially accelerated by the fact that the centrifugation chamber with the slightly detached and loosened upper part is now re-inserted in the centrifuge and is again briefly spun. Thereby the remaining sample fluid is pressed under the centrifugal pressure into the annular gap between the bottom edge (seal lip) of the upper part and the filter material therebelow, owing to which this filter material quickly fills up with the sample fluid and the sediment field is thereby dried in a particularly rapid manner.

An essential point here is that during the entire drying process the slide coated with the sediment need not be removed from the centrifugation chamber, so that conditions of absolute cleanness exist.

It is further important that also the subsequent treatment processes, such as staining of the dried sediment sample and fixing of the sediment sample, take place without removal of the sediment-covered slide from the centrifugation chamber.

Thus, such sediments can be produced in a particularly gentle manner without loss of delicate cells as test object, as was the case in the prior art. In the prior art, in fact, the slide covered by spontaneous sedimentation had to be removed from the known centrifugation chamber in order subsequently to continue the treatment of the sediment sample by immersion in various staining and fixing solutions. In these further treatment processes many of the cells to be tested were lost.

This is avoided by the present innovation.

Another feature of the present innovation is that the height of the annular space is less than the height of the filter material used, thereby ensuring that during the slight release of the tension between the upper part and the lower part, while the upper part moves slightly away from the lower part, the filter material compensates this difference in height and remains force-lockingly applied on the slide, thereby ensuring a good suction effect.

As clamping means for clamping the upper part to the lower part a number of designs enter into consideration, all of which are to be comprised under the present inventive idea.

In a first preferred embodiment it is provided that as clamping means a simple screw arrangement is used, the upper part having a male thread which engages in an associated female thread of the lower part and can be screwed therein.

With this embodiment, when releasing the clamping connection (unscrewing), a brief rotary movement is executed between the upper part and the underlying slide to be coated. In cases where this rotary movement is undesirable, it is provided in a second preferred embodiment that the upper part is to be set down on the lower part in vertical direction and that the clamping is effected with a cap nut. There would then be a collar with a male thread on the lower part, and on the upper part a cap nut would be rotatably mounted having a corresponding female thread. For clamping, the cap nut is then screwed by its female thread onto the externally threaded collar of the lower part, the two parts being again clamped together in vertical direction. A third preferred embodiment of a clamping means acting in vertical direction relates to an eccentric clamping means. Here there would be present, instead of the cap nut, an eccentric collet which has on the outer circumference slit type cutouts arranged in the manner of a coarse thread, into which associated extensions of the lower part engage. This eccentric clamping means may also be called a bayonet clamping means.

In the last-named embodiments (cap nut, eccentric clamping means and bayonet closure) there is no rotary movement between the upper and lower parts, because there is a third part (either the cap nut or the eccentric/-(bayonet sleeve).

All data and features disclosed in the documents—including the abstract—in particular the spatial organization illustrated in the drawings, are claimed as essential to the invention, insofar as, singly or in combination, they are novel over the prior art.

BRIEF DESCRIPTION OF THE DRAWING

In the following, the innovation will be explained more specifically with reference to drawings representing merely a mode of realization. Further essential features and advantages of the innovation will become evident from the drawings and their description.

DESCRIPTION OF THE PREFERRED EMBODIMENTS

The centrifugation chamber 1 consists essentially of a cylindrical upper part 2, which has an upper opening 5 for filling with the fluid to be tested. The fluid collects in the interior 6.

Figure 1:
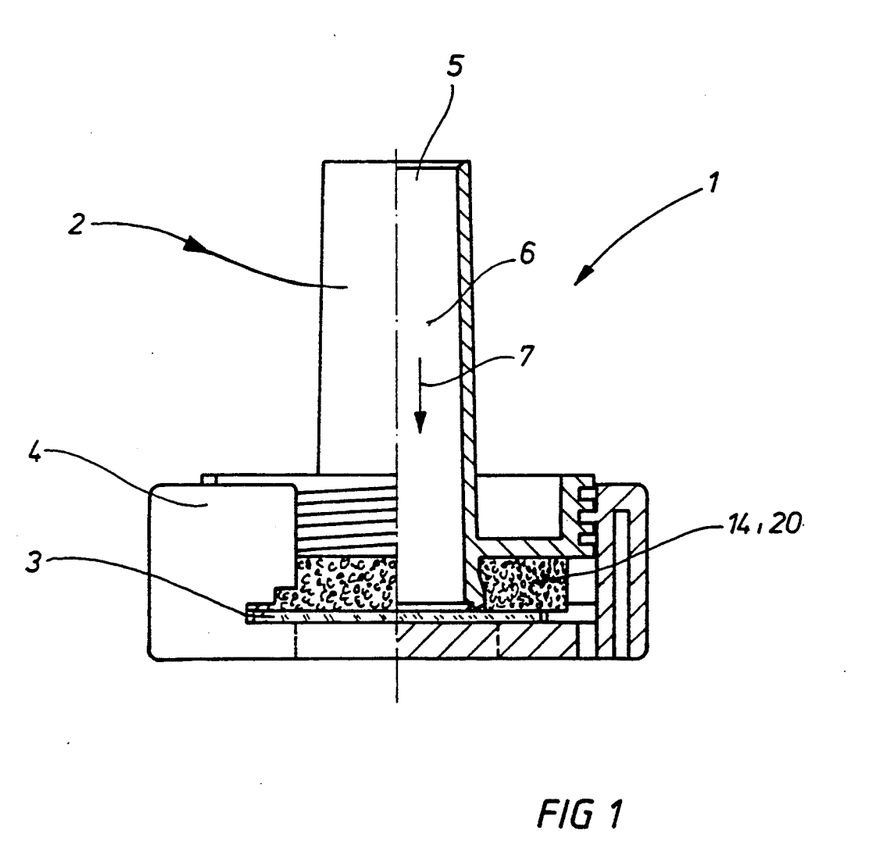
FIG. 1 shows schematically a side elevational view and a partial section through a centrifugation chamber according to the innovation.
Figure 5:
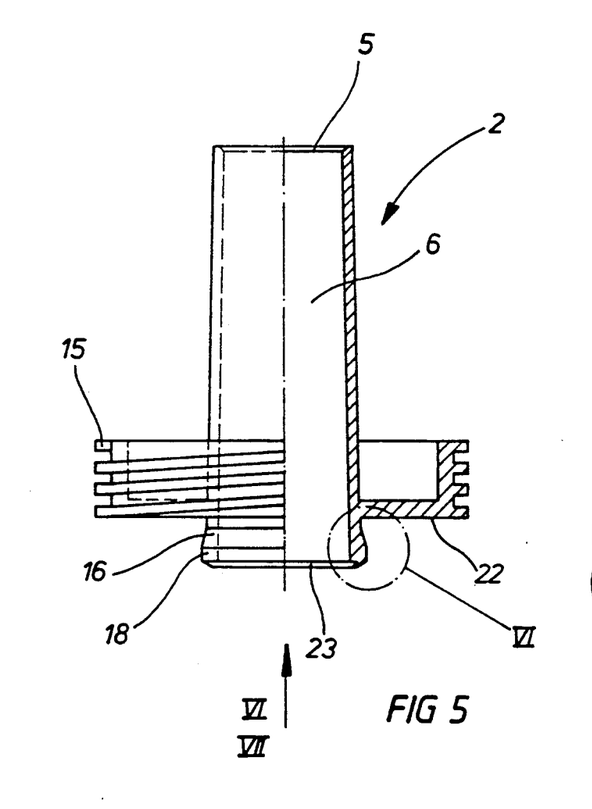
FIG. 5: the upper part in side view and partially in section.

According to FIGS. 1 and 5, the upper part 2 is slightly conical in the direction of the lower seal face 23.

The upper part 2 is screwed by its external thread 15 into the associated internal thread 10 (FIGS. 2,3) of the lower part 4, and according to FIG. 1 there is arranged at the lower shoulder 16 (FIGS. 6,7) of the upper part 2 a suction element 14 (FIGS. 8,9) which radially surrounds this shoulder 16 and is present in an annular space 20 formed between the upper part 2 and the lower part 4. The lower end face—constituting a seal face 23—of the upper part 2 rests, in the functional state of the centrifugation chamber 1 per FIG. 1, on a slide 3, which may selectively be formed as a round disk or as a rectangular glass body.

Figure 2:
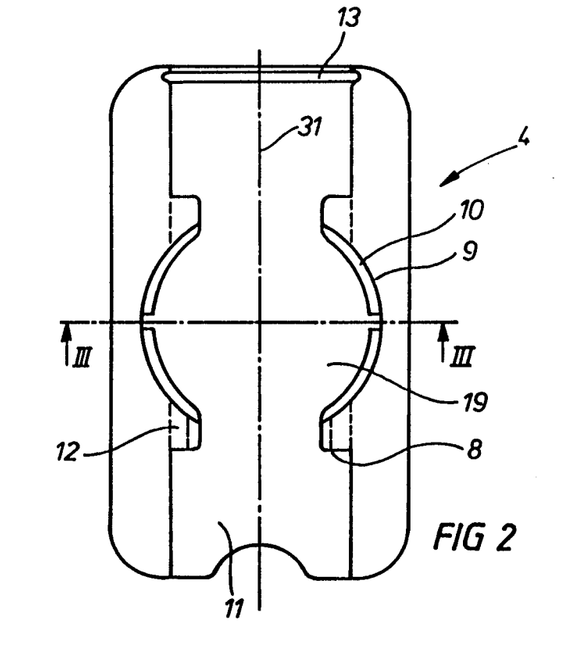
FIG. 2: top plan view of the lower part of the centrifugation chamber shown in FIG. 1.
Figure 3:
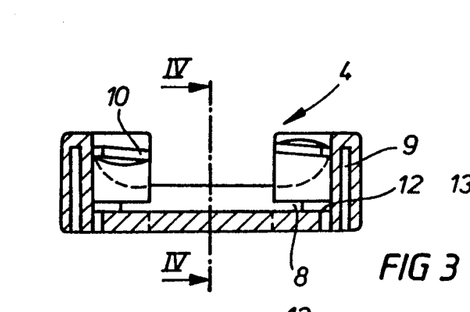
FIG. 3: section along line III—III in FIG. 2.
Figure 4:
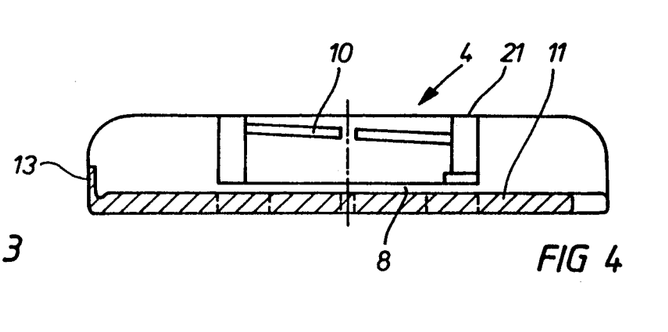
FIG. 4: section along line VI—VI in FIG. 3.

According to FIGS. 2 to 4, the lower part 4 is of plate-like form and is defined by a lower flat bottom plate 11 extending in longitudinal direction 31, in the center of which an internal thread 10 is integrally formed, which extends upward above the bottom plate 11.

In slide-in direction of the slide, the shoulder 9 with thread 10 is interrupted by slide-in openings 8, so that a rectangular slide is slipped on from below in FIG. 2 in longitudinal direction 31 onto the bottom plate 11 and in so doing is passed through the slide-in openings 8 until it strikes against an opposite shoulder 13 rising above the bottom plate 11.

A circular slide 3 is used, this slide can either be inserted from above on the bottom face 19, limited only by the thread 10, or it can selectively be inserted into the zone of the bottom face 19 through the front slide-in opening 8 in shoulder 9.

Figure 6:
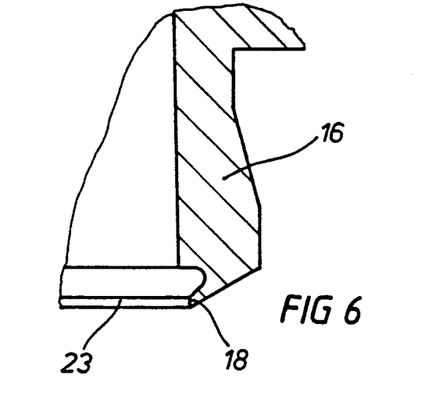
FIG. 6: a detail of FIG. 5 in a first form of realization.

For connecting the upper part 2 with the lower part 4 the upper part 2 has further an external thread 15, which in the embodiment example per FIGS. 1 to 5 is integrally formed on the upper part 2, the upper part 2 having downwardly extending a shoulder 16, The end face of shoulder 16 constitutes a seal face 23 and has an integrally formed seal lip 18 as shown in detail in FIG. 6.

Figure 7:
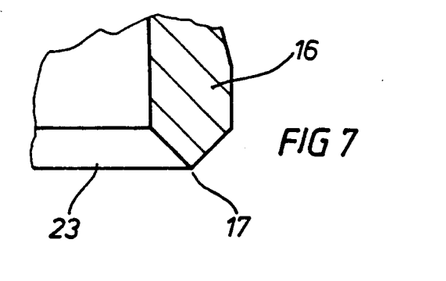
FIG. 7: the detail of FIG. 5 in a second form of realization.

In another form of realization, the seal lip 17 may be designed as an acute surface area.

In both cases the seal lip 17, 18 rests on the surface of slide 3 when the upper part 2 is screwed onto the lower part 4.

There forms then, radially outward of shoulder 16, an annular space 20 in the direction of the radially farther outward edge face on the inner side of shoulder 9, and in the region of this annular space 20 a suction element 14 may be arranged.

Figure 10A:
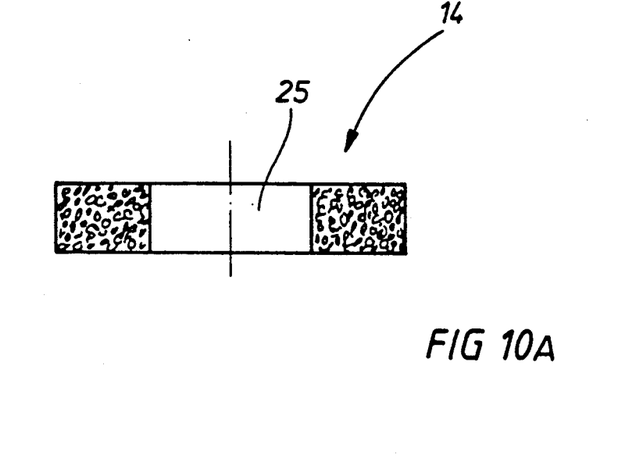
FIG. 10A is a side elevational view, in cross-section, of the suction element.
Figure 10B:
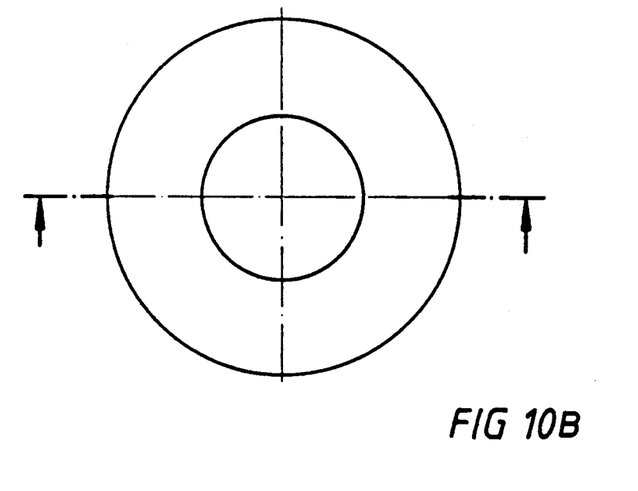
FIG. 10B is a top plan view of the suction element shown in FIG. 10A.

According to FIGS. 10A, 10B the suction element 14 is an annulus element and preferably consists of a sponge element.

Figures 8A, 8B, 9:
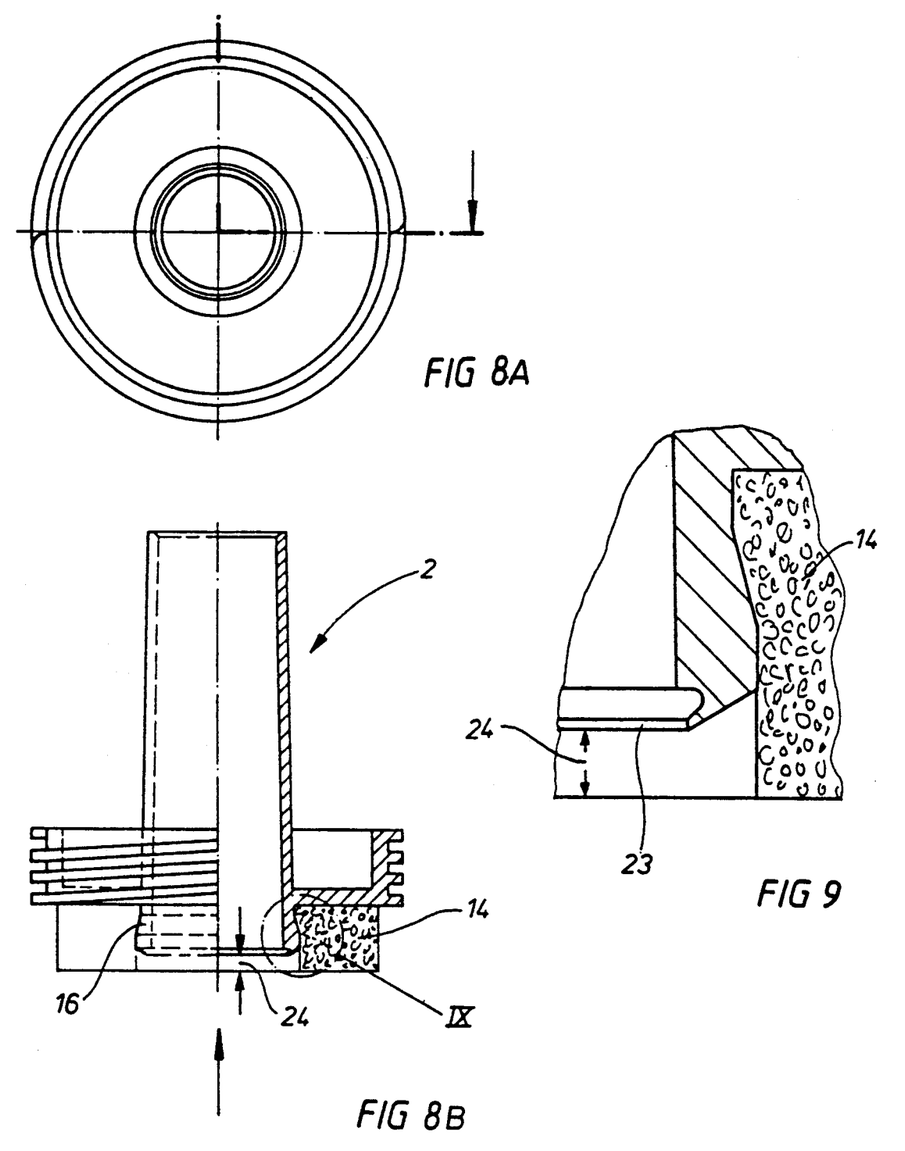
FIG. 8A is a top plan view of the upper part with a suction element arranged therein.
FIG. 8B is a side elevational view, partially in cross-section, of the suction element shown in FIG. 8A.
FIG. 9: a detail of FIGS. 8A, 8B.

What is important here is that according to FIGS. 8A, 8B and 9 the suction body 14 is higher than the height of shoulder 16, so that the suction element 14 protrudes over the bottom edge (seal face 23) of shoulder 16 by a distance 24.

This feature ensures that when the upper part 2 is screwed onto the lower part 4, the suction element 14 is compressed.

As the upper part 2 is being screwed onto the lower part 4, the seal lip 17,18 abuts sealingly on the surface of slide 3.

If no slide 3 is inserted, it may be provided that upon further screwing of the upper part 2 into the lower part 4 the abutment edge 22 on the underside of thread 15 at the upper part 2 strikes against an associated stop 21 in order to avoid damage to the thread 10,15 if the upper part 2 is screwed in forcibly.

What is important is that the entire centrifugation chamber 1 is suitable for insertion in a centrifuge and that a plurality of such centrifugation chambers can be inserted in a centrifuge suspension.

A further feature is that different test volumes can be used, simply because a single lower part 4 can be combined with different size upper parts 2.

For example, the upper part may have a diameter of 12.4 mm just as well as a diameter of e.g. 17.5 mm.

The different size upper parts 2 can then be used with one and the same lower part 4.

The sliding in of a slide on the bottom plate 11 is limited by guide ribs 12 laterally delimiting the bottom face 19.

It is further important that the recess 25 is placed tightly on the shoulder 16 of the upper part 2, so that when unscrewing the upper part 2 from the lower part 4 the suction element 14 is removed with the upper part 2, thereby avoiding impairment of the now coated slide 3.

At the start of a test, the upper part 2 is filled through the opening 5 with the liquid to be tested, which collects in the interior 6.

The entire centrifugation chamber 1 is then inserted, possibly together with additional centrifugation chambers, into the suspension of a centrifuge and is spun. The heavier particles of the liquid to be tested migrate downwardly in arrow direction 7 and deposit on the surface of slide 3.

Figure 11:
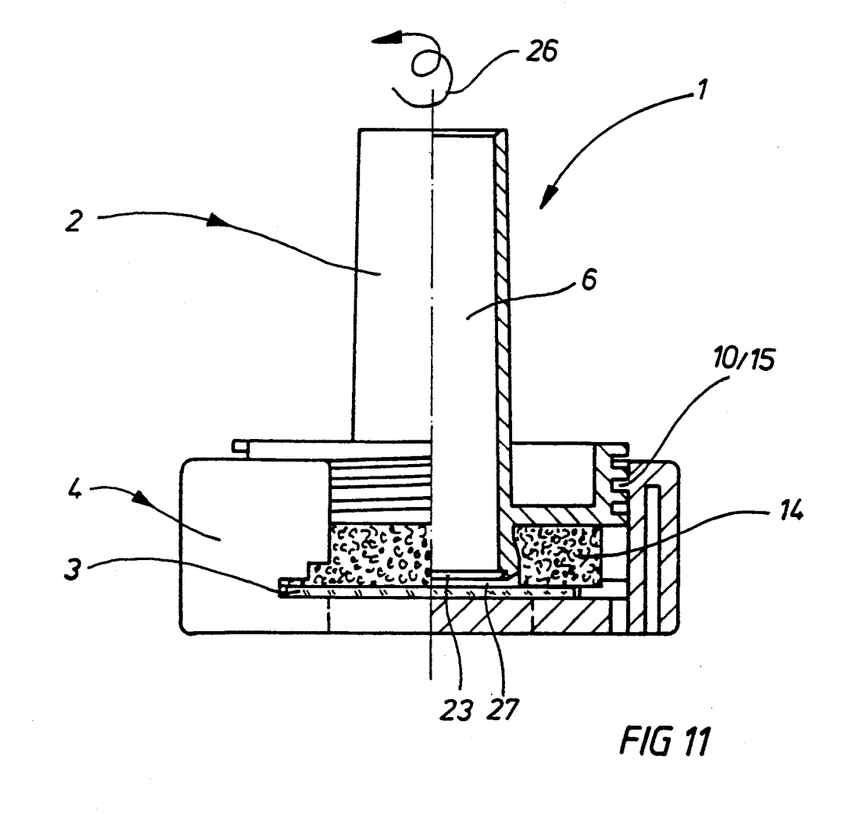
FIG. 11: the centrifugation chamber per FIG. 1 in a second functional state.

Now to remove the still remaining liquid, the upper part 2 is, according to FIG. 11, slightly unscrewed from the lower part 4 in arrow direction 26, so that a flow gap 27 forms between the seal face 23 and the top side of slide 3.

The liquid still present in the interior 6 now migrates slowly (according to the size of the flow gap 27) radially outwardly in the direction of the suction element 14, which absorbs this liquid.

It is important that the coating of slide 3 due to the sedimentation that has occurred is not disturbed, for according to the size of the flow gap 27 the outflow of the remaining liquid into the suction element 14 can be controlled very precisely and with time delay.

By releasing the upper part 2 from the lower part 4 according to FIG. 11, the suction element 14 relaxes, so that it is able to absorb more liquid than before, where—according to FIG. 1—it was compressed.

As soon as no further liquid migrates from the interior 6 into the suction element 14, the upper part 2 can be unscrewed completely in arrow direction 26 and slide 3 taken out.

Extraction occurs either upward (with the upper part 2 lifted off) or in longitudinal direction 31 through the slide-in openings 8.

Figure 12:
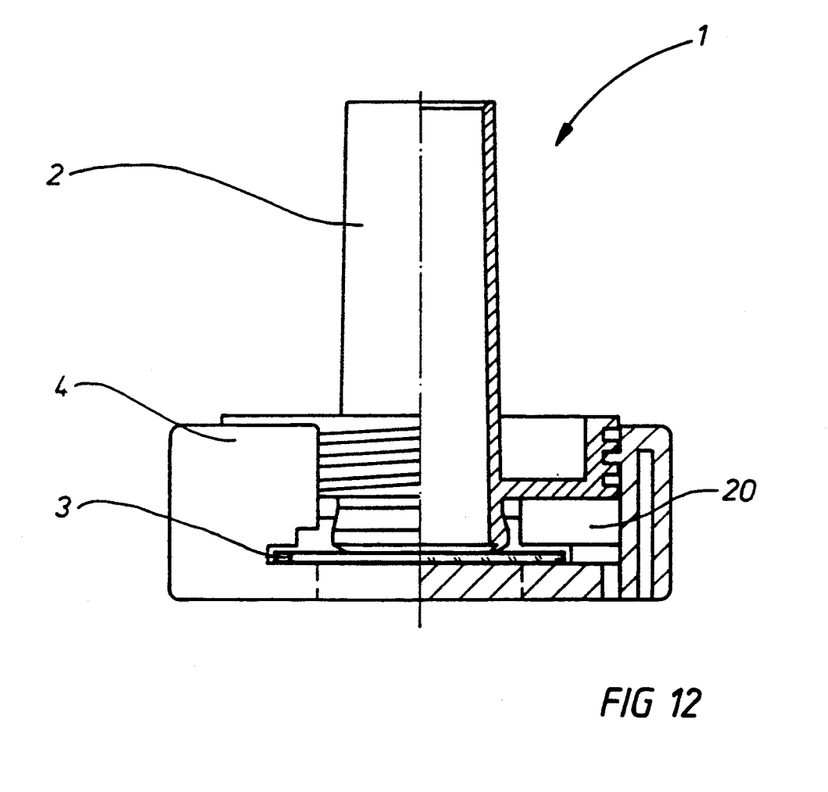
FIG. 12: the centrifugation chamber per FIG. 1 without suction element.

For other test procedures the suction element 14 may be omitted entirely. Such a test arrangement is shown in FIG. 12. It can be seen there that an annular space 20 is formed at the radial outer circumference of shoulder 16 of the upper part 2.

With this design it is possible to remove the test liquid still remaining in the interior 6 with a pipette or the like.

Figure 13:
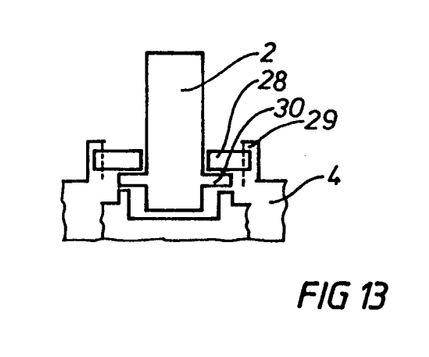
FIG. 13: schematized, a further representation of a clamping means between the upper and lower parts of the centrifugation chamber.

FIG. 13 shows as additional embodiment the presence of a threaded nut 28, which is screwed by its external thread onto an associated internal thread 29 in the region of the shoulder 9 of the lower part 4. The clamping between upper part 2 and lower part 4 is effected in that fixed to the upper part 2 an annular flange 30 directed radially outward is provided which abuts against an associated edge on the housing (stop 21).

I claim:

1. Centrifugation chamber for liquid testing comprises a first part in the form of a vessel having an open end defining a sealing lip; a second part for receiving a slide on which a sediment sample is to be deposited from the liquid; a slide received in the second part; attaching means for attaching said first and second parts to place said sealing lip in abutment against the slide to form a liquid seal; and absorbing means provided about said sealing lip for absorbing the liquid within said vessel when the liquid seal is broken by separation of said sealing lip from the slide, whereby said first and second parts may be separated from each other with minimum disturbance to the sediment sample on the slide and spillage of the liquid.

2. Centrifugation chamber as defined in claim 1, wherein said attaching means comprises a male threaded portion on said first part and a female threaded portion on said second part.

3. Centrifugation chamber as defined in claim 1, wherein said first part includes an annular flange, and said attaching means comprises a threaded nut rotably retained on said first part in abutment against said annular flange, and is screwed into an associated threaded part on said second part to advance said sealing lip into abutment against the slide.

4. Centrifugation chamber as defined in claim 1, wherein said attaching means comprises a bayonet closure acting between said first and second parts.

5. Centrifugation chamber as defined in claim 1, wherein an annular space is formed about said sealing lip when said first and second parts are attached to each other, and said absorption means is arranged within said annular space.

6. Centrifugation chamber as defined in claim 1, wherein said second part has a slide receiving means for receiving both round and rectangular slides.

7. Centrifugation chamber as defined in claim 1, wherein said first and second parts are made of plastic.

8. Centrifugation chamber as defined in claim 1, wherein said absorbing means comprises an annular shaped sponge surrounding said vessel proximate to said sealing lip.

9. Centrifugation chamber as defined in claim 8, wherein said sponge projects beyond said sealing lip in a relaxed state when said first and second parts are moved relative to each other to at least partially separate said sealing lip and said slide, and is compressed into an annular space about said sealing lip when said sealing lip is placed into abutment against the slide.

* * * * *